United States Patent [19]
Shiao et al.

[11] Patent Number: 5,057,224
[45] Date of Patent: Oct. 15, 1991

[54] METHOD FOR EVALUATING THE PERFORMANCE OF REVERSE PHASE HIGH PERFORMANCE LIQUID CHROMATOGRAPHIC COLUMNS

[75] Inventors: Ming-Shi Shiao; Lee-Julian Lin, both of Taipei, Taiwan

[73] Assignee: National Science Council, Taipei, Taiwan

[21] Appl. No.: 507,455

[22] Filed: Apr. 11, 1990

[51] Int. Cl.$^5$ .............................................. B01D 15/08
[52] U.S. Cl. .................................. 210/635; 210/656; 210/198.2; 73/61.1 C
[58] Field of Search ...................... 210/635, 656, 198.2; 55/67, 386; 73/61.1 C; 436/161

[56] References Cited

PUBLICATIONS

Smith, "Characterization of Reversed-Phase Liquid Chromatography Columns with Retention Indexes of Standards Based on an Alkyl Aryl Ketone Scale", Anal. Chem., 1984, 56, pp. 250-262.

Kikta, "Phenones: A Family of Compounds Broadly Applicable to Use as Internal Standards in High Performance Liquid Chromatography", Journal of Chromatography, 1977, 138, pp. 41-45.

Shiao et al., "Two New Triterpenes", Journal of Natural Products, 886-890, Sep.-Oct., 1987.

Shiao et al., "Teiterpenes in Ganoderma Lucidum", Phytochemistry, 27, 3, 873-875, 1988.

Lin et al., "Triterpenes From Ganoderma Lucidum", Phytochemistry, 27, 7, 2269-2271, 1988.

Primary Examiner—Ernest G. Therkorn
Attorney, Agent, or Firm—Bacon & Thomas

[57] ABSTRACT

The present invention provides a composition for evaluating the performance of reverse phase high performance liquid chromatographic columns, especially in the aspect of separating a mixture having stereo- and positional isomers, which comprises oxygenated triterpenoids obtained from the cultured mycelia of *Ganoderma lucidum* (Fr.) Karat.

1 Claim, 7 Drawing Sheets

METHOD FOR EVALUATING THE PERFORMANCE OF REVERSE PHASE HIGH PERFORMANCE LIQUID CHROMATOGRAPHIC COLUMNS

TECHNICAL FIELD OF THE INVENTION

The present invention relates to a method and compositions for evaluating the performance of reverse phase high performance liquid chromatographic columns.

BACKGROUND OF THE INVENTION

High performance liquid chromatography (HPLC) is a very common practice in analyzing bioactive materials, drug, toxic materials and metabolites, et al. In practice, a reverse phase high performance liquid chromatographic column is adopted by most people in the art. However, reverse phase high performance liquid chromatographic columns are relatively expensive and have a certain periods of operative life, moreover a reverse phase HPLC column marketed by different manufacturers will have different characteristics, therefore a quick and effective method for evaluating the performance thereof is desired for the operators.

The separating performance of a reverse phase HPLC column is commonly expressed by resolution R, which is dependent on the capacity factor K', separation factor $\alpha$ and theoretical plate number N. The resolution R can be simply calculated:

$$R = 0.25[(\alpha - 1)/\alpha] \sqrt{N} \ [K'/(K' + 1)]$$

The higher the R value, the better the resolution.

At present, the standards used for testing the reverse phase HPLC columns performances are varied between different manufacturers. A composition comprising aromatic compounds such as benzene, naphthalene, toluene, anthracene, methyl benzoate, and the like is the type of standards most commonly used. The compounds contained in this type of standards have the same functionality and only deviate in polarity, consequently they are limited to evaluate the capacity factor, peak symmetry and to calculate the theoretical plate number.

R. M. Smith in his article, entitled "Characterization of Reversed-Phase Liquid Chromatography Columns with Retention Indexes of Standards Based on an Alkyl Aryl Ketone Scale." *Anal. Chem.*, 56, 256 (1984), discloses an improved composition for evaluating the reverse phase HPLC columns comprising different functionality compounds as its components such as p-cresol, nitrobenzene, 2-phenylethanol and toluene. However, the difference in functionality between these constituting components does not have a well designed regularity.

An article by E. J. Kikta, Jr., et al. entitled "Phenones: A Family of Compounds Broadly Applicable to Use as Internal Standards in High-Performance Liquid Chromatography." *J. Chromatogr.*, 138, 41 (1977), discloses another standards for evaluating the reverse phase HPLC columns, which comprises alkylphenones each having various chain length. The alkylphenones all have the same ketone functionality but different polarities due to the various chain lengthes of the alkyl chains.

Therefore, none of the standards for evaluating the performance of the reverse phase HPLC columns comprises compounds each having multiple functionalities, compounds being paired stereo isomers, and compounds being paired positional isomers, which is not only able to be used for evaluating the performance of the reverse phase columns in general aspect but in the aspect of separating stereo- and positional isomers.

The main purpose of the present invention is to provide a composition for evaluating the performance of reverse phase HPLC columns in both the conventional aspect and the aspect of separating stereo- and positional isomers.

Another purpose of the present invention is to provide a method for evaluating the performance of reverse phase HPLC columns.

SUMMARY OF THE INVENTION

The composition for evaluating the performance of reverse phase HPLC columns provided in present invention comprises the oxygenated triterpenoids having the formula

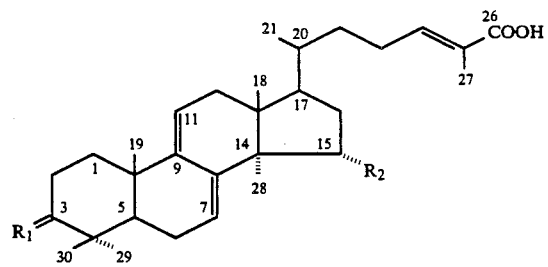

wherein:

| Compounds | $R_1$ | $R_2$ |
|---|---|---|
| 1 | OH, H | OH |
| 2 | H, OH | OH |
| 3 | OH, H | OAc |
| 4 | H, OH | OAc |
| 5 | OAc, H | OH |
| 6 | H, OAc | OH |
| 7 | OAc, H | OAc |

| Compounds | R₁ | R₂ |
|---|---|---|
| 8 | H | OAc |
|   | ⬥OAc |   |

$$Ac = CH_3\overset{O}{\underset{\|}{C}}-.$$

There are eight oxygenated triterpenoids contained in the composition, wherein 1/2, 3/4, 5/6, and 7/8 four pairs are C-3 stereoisomers and have a descending polarity as the number increases due to the hydroxyl functional groups thereof being acetylated, the compounds 3/5 and 4/6 are C-3/C-15 positional isomers.

The composition according to present invention comprises paired stereoisomers and positional isomers each having multiple functional groups and varied polarities, which serve as an improved test standards to evaluate the performance of commercially available reversed phase liquid chromatographic columns.

DETAILED DESCRIPTION OF THE INVENTION

Figure 1:
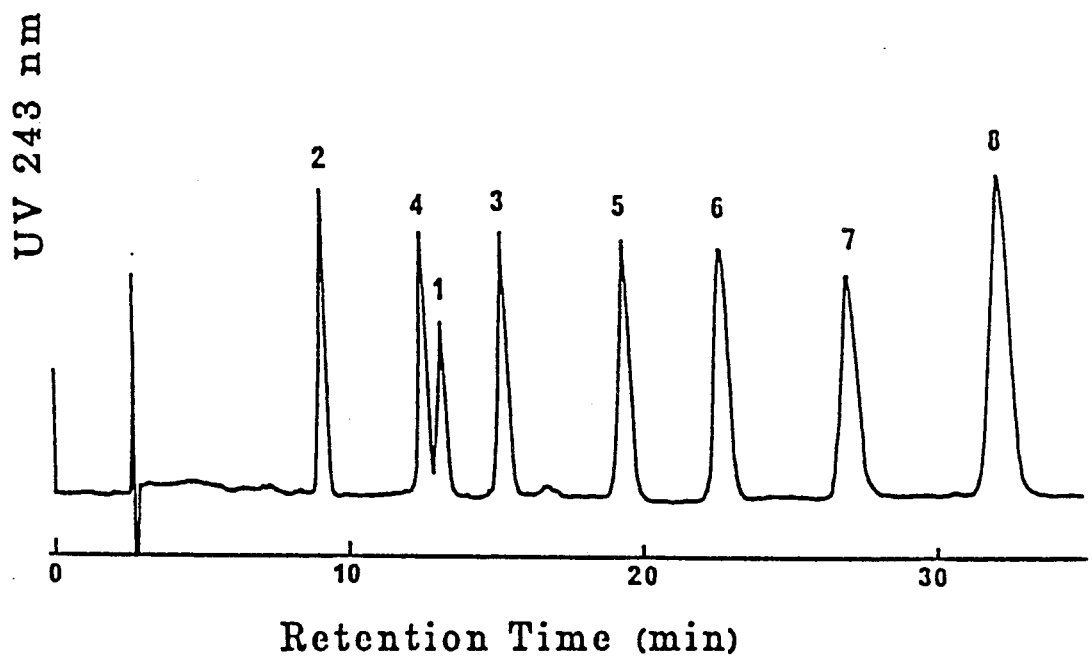
FIG. 1 is a reverse-phase HPLC chromatogram of the compounds 1-8 mentioned above in methanol-water-acetic acid (85:15:0.5, v/v); flow rate, 1.0 ml/min.

The present invention provides a composition for evaluating the performance of reverse phase high performance liquid chromatographic columns, which comprises the oxygenated triterpenoids obtained from the cultured mycelia of G. lucidum (Fr.) Karst having the formula:

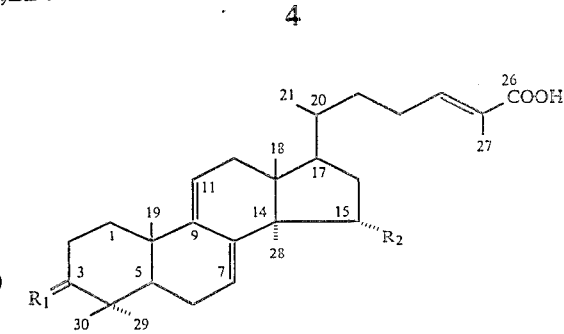

wherein:

| Compounds | R₁ | R₂ |
|---|---|---|
| 1 | OH | OH |
|   | ⬥H |   |
| 2 | H | OH |
|   | ⬥OH |   |
| 3 | OH | OAc |
|   | ⬥H |   |
| 4 | H | OAc |
|   | ⬥OH |   |
| 5 | OAc | OH |
|   | ⬥H |   |
| 6 | H | OH |
|   | ⬥OAc |   |
| 7 | OAc | OAc |
|   | ⬥H |   |
| 8 | H | OAc |
|   | ⬥OAc |   |

$$Ac = CH_3\overset{O}{\underset{\|}{C}}-.$$

The 8 components of the composition are paired stereoisomers and positional isomers, and the polarities between each pair of isomers are varied gradually. The particular features of the present invention composition are further described in the following:

1) The 8 components have hydroxyl/acetoxyl functional groups and carboxylic acid functional groups, which can be used as a whole to undergo a whole range evaluation or can be tailored to several pairs of isomers as desired.

2) Among the 8 components, 1/2, 3/4, 5/6 and 7/8 are four pairs of C-3 stereoisomers, and the polarity thereof descends as the number increases. Therefore, the K' and α values of the two isomers of each pair provide the information for evaluating the resolution of reverse phase columns with respect to stereoisomers, as well as the K' and α values between each pair of isomers are useful to evaluate the effect of varying polarity on the performance of reverse phase columns.

3) Components 3/5 and 4/6 are two pairs of C-3/C-15 positional isomers. The K' and α values of the two isomers of each pair are useful for evaluating the resolution of reverse phase columns with respect to positional isomers.

4) The 8 components all have a transoid conjugated diene skeleton in its cyclic structure and the same C-17 side chain, therefore they have common UV absorbances (in MeOH, log ε of UV243 nm is about 4) and can be monitored by an UV detector at a wavelength of 235, 243 and 252 nm.

5) The distribution of the polarities of these 8 components falls in a suitable range with respect to the conventional reverse phase liquid chromatography operation conditiuis (the eluents used for example are methanol, acetonitrile, or tetrahydrofuran aqueous mixture), which causes the capacity factors K' of the components fall in a feasible range for completing the reverse phase HPLC test within a reasonable periods of time.

6) The chemical properties of the 8 components are substantially stable, which renders them to be safely stored in a relative long term.

Compounds 1–8 were obtained from the cultured mycelia of fungus Ganoderma lucidum (Fr.) Karst. The isolation and purification procedures of these compounds have been reported previously in:

1.) "Two new triterpenes of the fungus Ganoderma lucidum", Shiao, M.-S.; Lin, L.-J. J. of Natural Products 1987, 50, 886.

2.) "Triterpenes in Ganoderma lucidum", Shiao, M.-S.; Lin, L.-J.; Yeh, S.-F. of Phytochemistry 1988, 27, 873.

3) "Triterpenes from Ganoderma lucidum", Shiao, M.-S.; Lin, L.-J.; Yeh, S.-F. of Phytochemistry 1988, 27, 2269.

The composition of present invention is particularly suitable for evaluating the performance of reverse phase HPLC columns in separating compounds containing stereo- or positional isomers, such as steroids and metabolites; Eiconsanoid-type compounds and metabolites, et al. Using the composition of present invention to evaluate a $C_{18}$ reverse phase HPLC column, e.g. 0.4×25 cm; 5,7 or 10 μM, the mobile phase is a binary mobile phase containing considerable volumn percentage of water with methanol or acetonitrile, The following examples are provided to illustrate the invention and not meant to be limiting.

EXAMPLE 1

The purpose of this example is to illustrate that the composition of present invention can be subjected to conventional reverse phase liquid chromatography operation, and this operation finishs within a reasonable periods of time.

Figure 2:
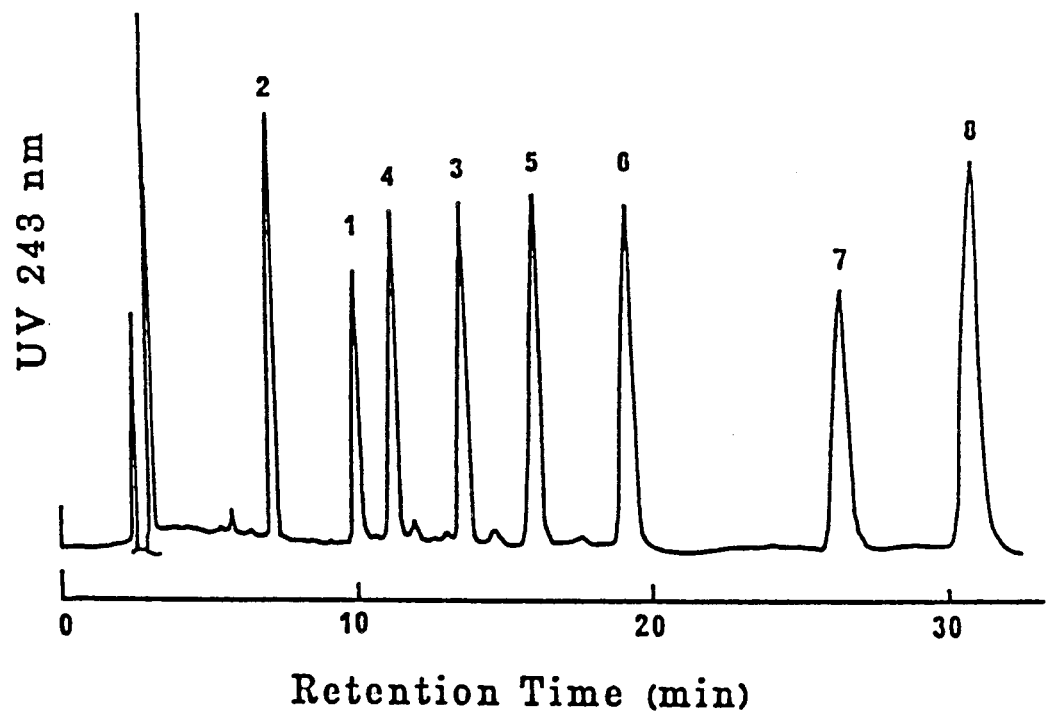
FIG. 2 is a reverse-phase HPLC chromatogram of the compounds 1-8 mentioned above in acetonitrile-water-acetic acid (80:20:0.5, v/v); flow rate, 1.0 ml/min.

Solvents were HPLC-grade methanol and acetonitrile (Labscan, Dublin, Ireland). The HPLC system consisted of a Familic-300S (Jasco, Tokyo, Japan) solvent delivery system equipped with a Model 7125 sample injector (Rheodyne, Berkeley, U.S.A.), a UVIDEC-100-V variable wavelength UV detector (Jasco), and an RC-250 recorder (Jasco). A prepacked reverse phase column, 25×0.46 cm, 5 μm (Cosmosil 5$C_{18}$), was obtained from Nacalai (Kyoto, Japan). The mobile phases for eluting this composition were methanol-water-acetic acid (85:15:0.5, v/v) and acetonitrile-water-acetic acid (80:20:0.5, v/v), in which the low, fixed volume percentage of acetic acid (0.5%, v/v) was added to the binary mobile phases in order to maintain the oxygenated triterpenoids in the free acid form predominately. The flow rate is set at 1 ml/min.; and UV 243 nm is chosen. The chromatograms are shown in FIG. 1 and FIG. 2, respectively.

The $C_8$ reverse phase HPLC columns can also be evaluated by the composition of present invention, provided that the polarity of the mobile phase system is adjusted to have a relative higher value by varying the components of the mobile phase.

EXAMPLE 2

Two comercially available reverse phase HPLC columns, namely "A" brand and "B" brand were evaluated in this example.

Figure 3:
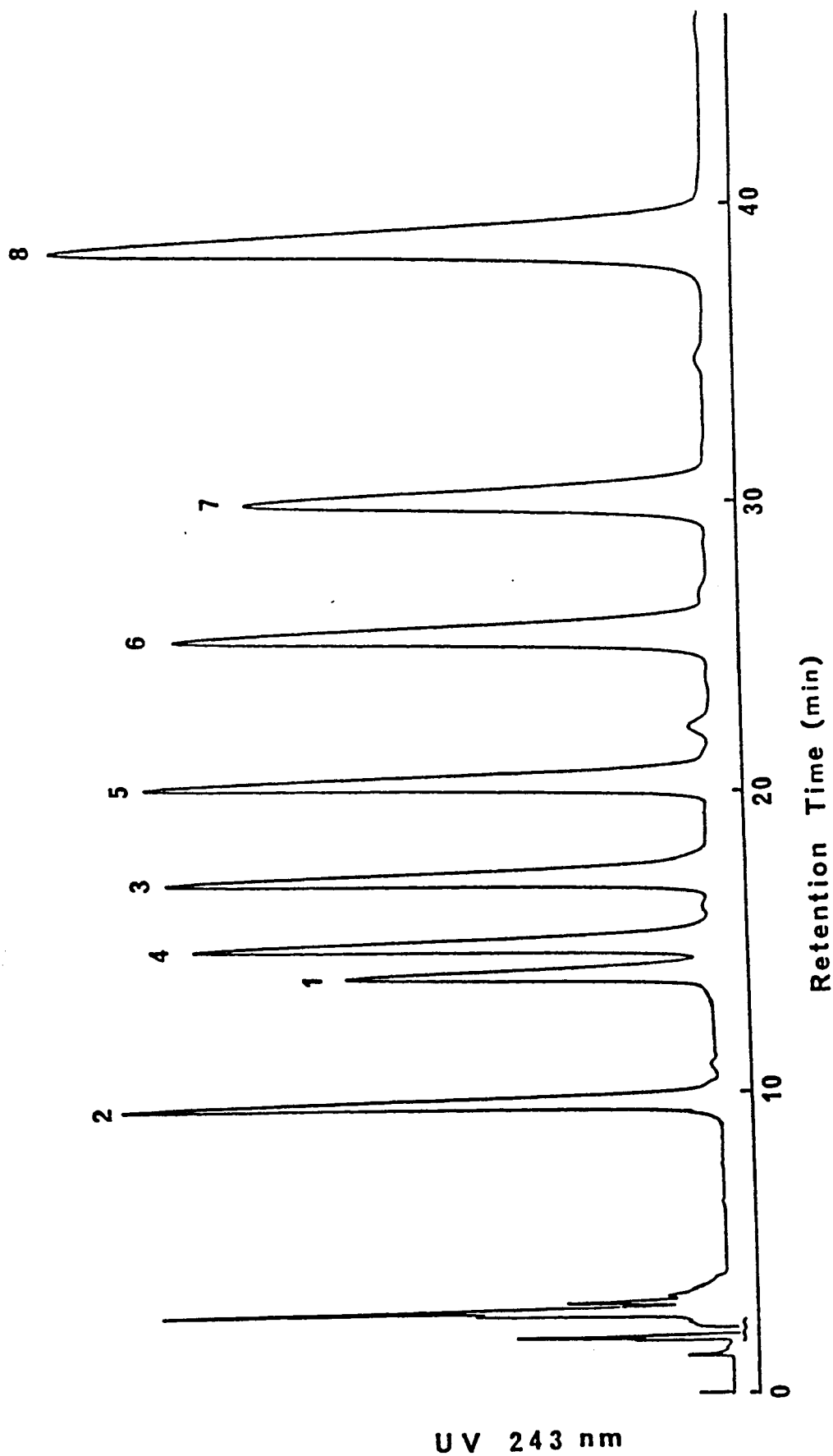
FIG. 3 is a reverse-phase HPLC chromatogram of the compounds 1-8 mentioned above in methanol-water-acetic acid (85:15:0.5, v/v); via "A" brand reverse phase column; flow rate, 1.0 ml/min.
Figure 4:
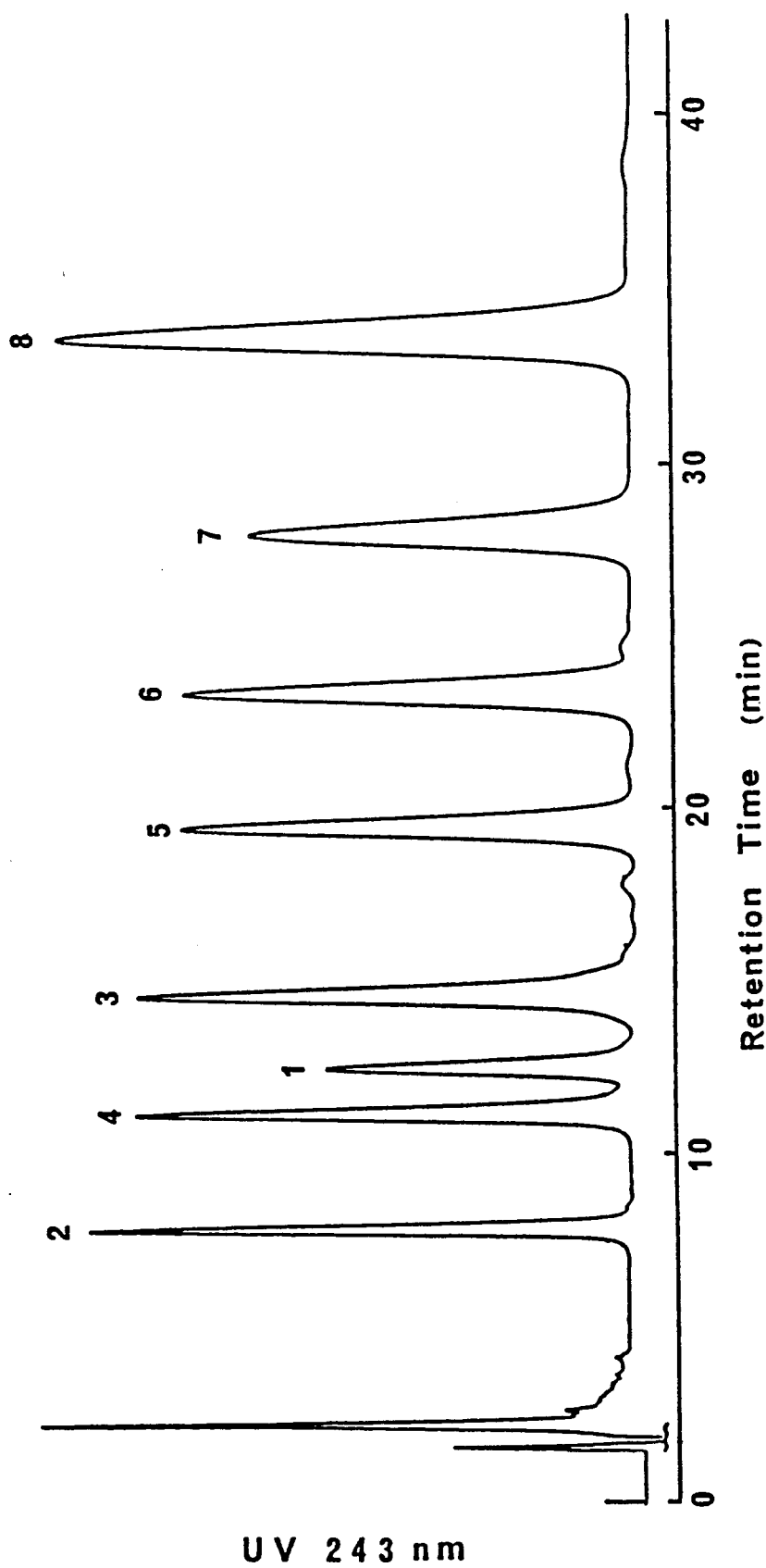
FIG. 4 is a reverse-phase HPLC chromatogram of the compounds 1-8 mentioned above in methanol-water-acetic acid (85:15:0.5, v/v); via "B" brand reverse phase column; flow rate, 1.0 ml/min.
Figure 5:
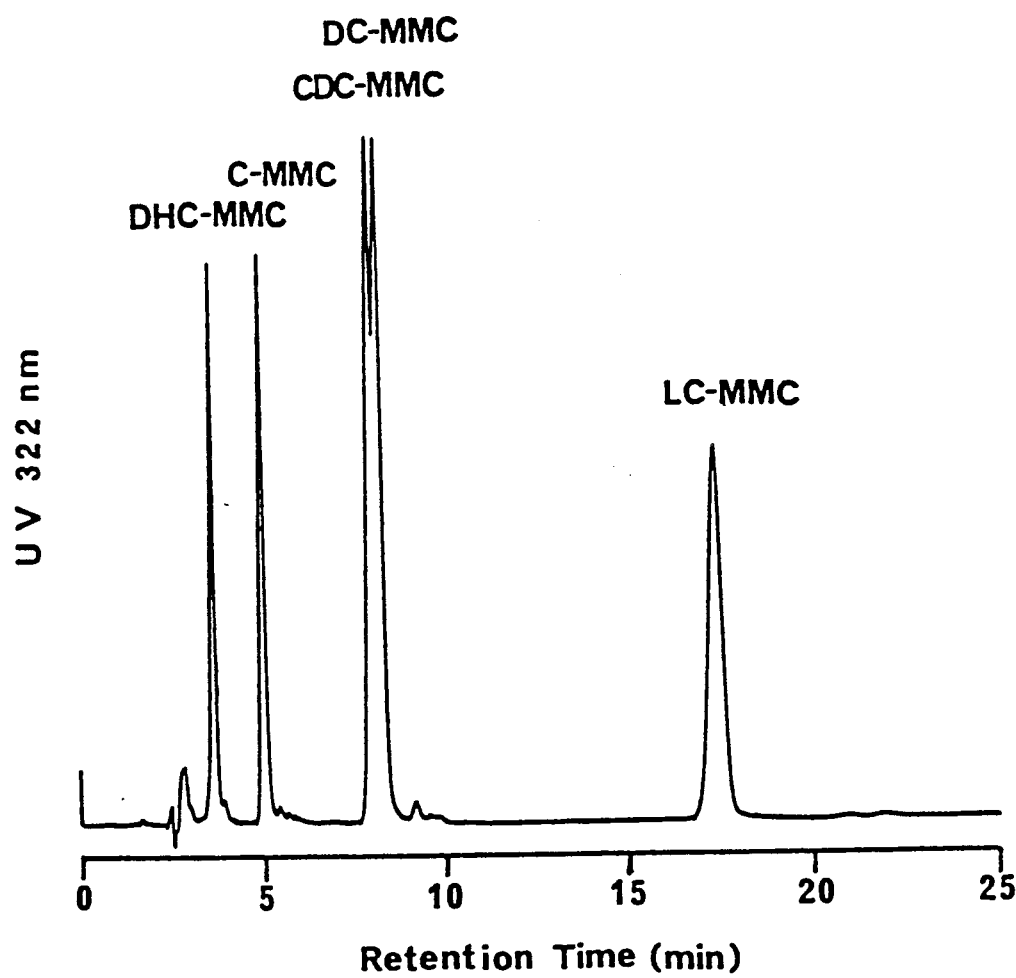
FIG. 5 is a reverse-phase HPLC chromatogram of the MMC derivatives of bile acids in acetonitrile-water (90:10, v/v); via "A" brand reverse phase column; flow rate, 1.0 ml/min. (MMC derivatives are the compounds derived frim 4-bromomethyl-7-methoxycoumarin).
Figure 6:
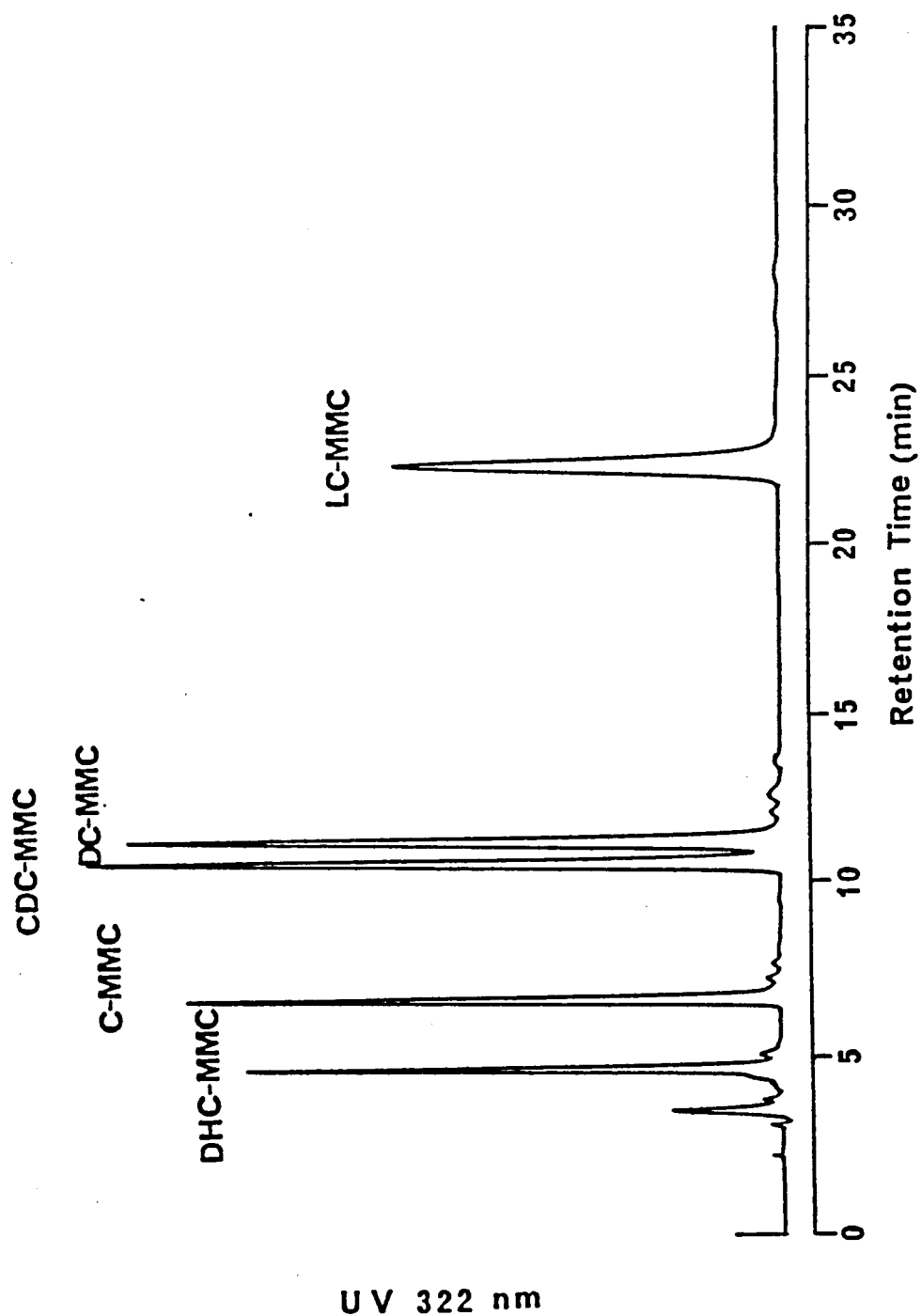
FIG. 6 is a reverse-phase HPLC chromatogram of the MMC derivatives of bile acids in acetonitrile-water (90:10, v/v); via "B" brand reverse phase column; flow rate, 1.0 ml/min.
Figure 7:
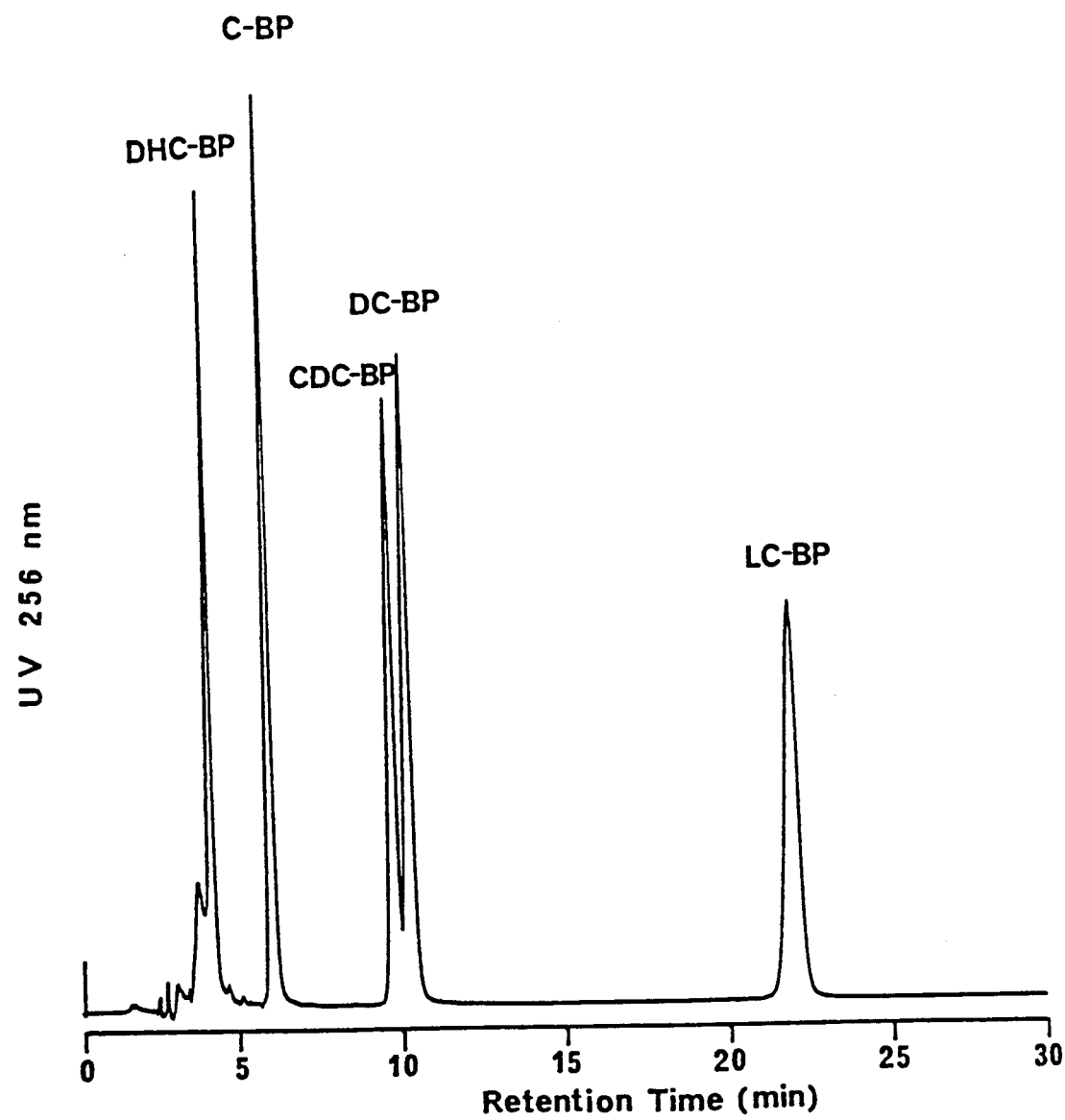
FIG. 7 is a reverse-phase HPLC chromatogram of the BP derivatives of bile acids in acetonitrile-water (90:10, v/v); via "A" brand reverse phase column; flow rate, 1.0 ml/min. (BP derivatives are the compounds derived from α, p-dibromo-acetophenone).
Figure 8:
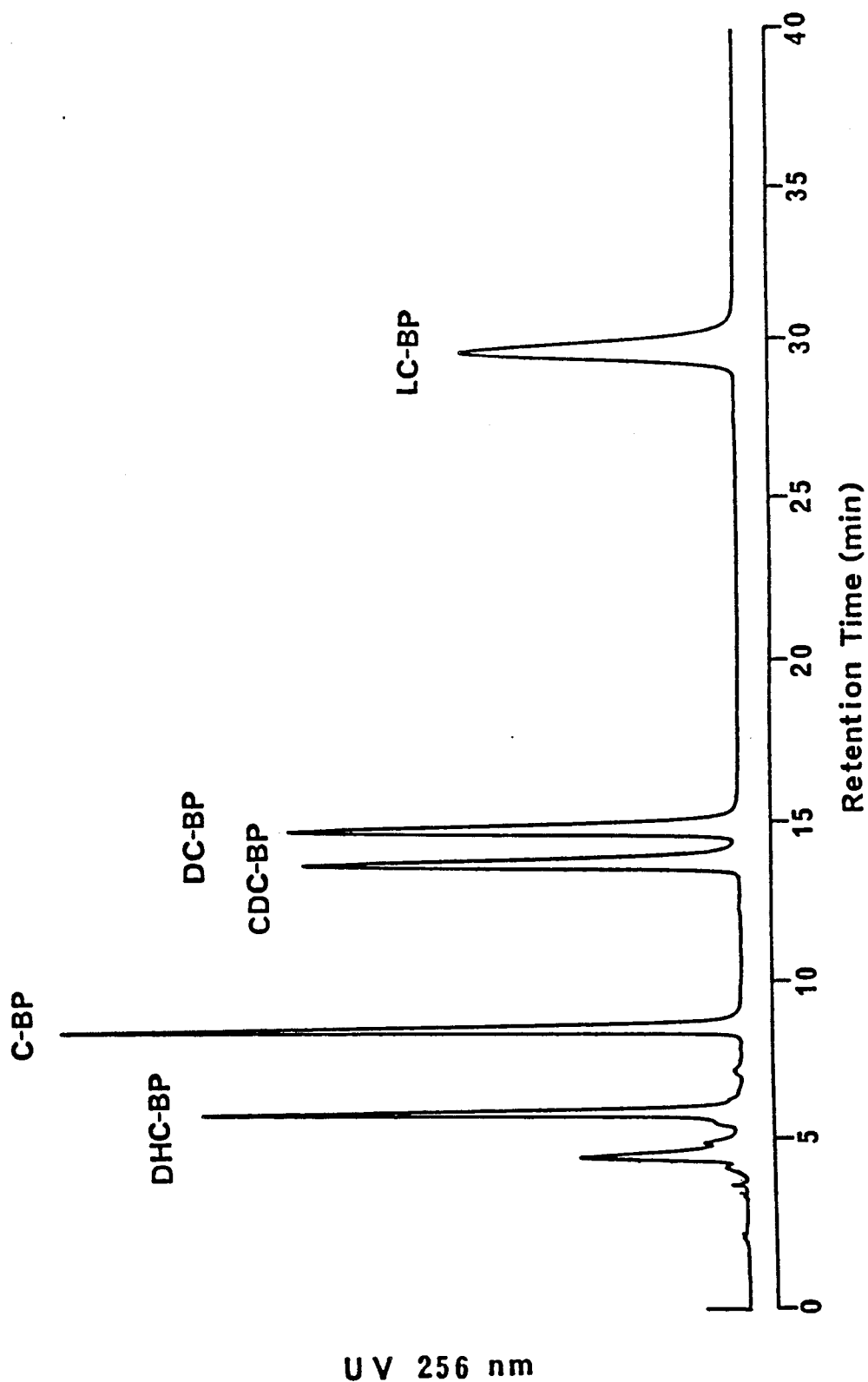
FIG. 8 is a reverse-phase HPLC chromatogram of the BP derivatives of bile acids in acetonitrile-water (90:10, v/v); via "B" brand reverse phase column; flow rate, 1.0 ml/min.

These two columns were evaluated under the identical operation conditions by using the composition of present invention as testing standards. The same HPLC system as in Example 1 was used except that the reverse phase column was replaced. The conditions and results are shown in FIG. 3 and 4, which illustrate that that "B" brand reverse phase column has higher separation facors (α) than those given by the "A" brand column.

EXAMPLE 3

This example illustrates that the "B" brand reverse phase column has a better resolution than "A" brand reverse phase column in above Example 1 when they are utilized in a reverse phase HPLC system to elute a mixture.

Two mixtures are to be separated in this example, each mixture contains 4-(Bromomethyl)-7-methoxycoumarin (abbreviated as MMC) derivatives and α, p-dibromo-acetophenone (abbreviated as BP) derivatives of the bile acids compounds having the following formula, respectively:

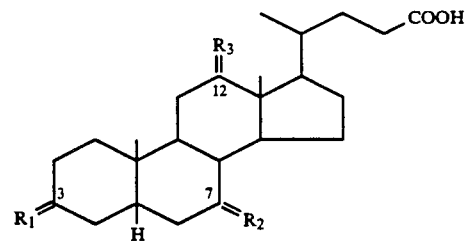

wherein:

| | $R_1$ | $R_2$ | $R_3$ |
|---|---|---|---|
| C | OH ⋮H | OH ⋮H | OH ⋮H |
| CDC | OH ⋮H | OH ⋮H | H ⋮H |
| DC | OH ⋮H | H ⋮H | OH ⋮H |
| LC | OH ⋮H | H ⋮H | H ⋮H |

| | $R_1$ | $R_2$ | $R_3$ |
|---|---|---|---|
| DHC | = O | = O | = O |

C represents cholic acid, CDC represents chenodeoxycholic acid, DC represents deoxycholic acid, LC represents lithocholic acid, and DHC represents dehydrocholic acid. These two mixtures were eluted under the identical reverse phase HPLC conditions ($CH_3CN:H_2O=9:1$, v/v; Flow rate=1 ml/min.) by using the same HPLC system as described in Example 1.

The results are shown in FIG. 5, 6, 7 and 8. As it can be seen from these figures, "B" brand reverse column does have a better performance than "A" brand reverse column in separating CDC-MMC/DC-MMC and CDC-BP/CD-BP isomers. Moreover, DC-BP/CDC-BP isomers are isolated completely via the use of "B" brand reverse column, which is not observed in "A" brand reverse column case. This results are agreed with the evaluation of above Example 2.

We claim:

1. A method for evaluating the performance of reverse phase high performance liquid chromatographic columns comprising subjecting a composition comprising the oxygenated triterpenoids having the formula

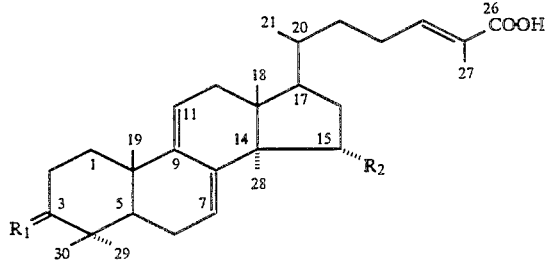

wherein:

| Compounds | $R_1$ | $R_2$ |
|---|---|---|
| 1 | OH | OH |
| | ⋮H | |
| 2 | H | OH |
| | ⋮OH | |
| 3 | OH | OAc |
| | ⋮H | |
| 4 | H | OAc |
| | ⋮OH | |
| 5 | OAc | OH |
| | ⋮H | |
| 6 | H | OH |
| | ⋮OAc | |
| 7 | OAc | OAc |
| | ⋮H | |
| 8 | H | OAc |
| | ⋮OAc | | wherein Ac is $CH_3\overset{\underset{\|}{O}}{C}-$ to reverse phase high performance liquid chromatography and evaluating the performance of the reverse phase high performance liquid chromatography columns based upon the results of subjecting said columns to said composition.

* * * * *